United States Patent [19]

Kobayashi et al.

[11] Patent Number: 5,363,314
[45] Date of Patent: Nov. 8, 1994

[54] FUEL CHARACTER JUDGING SYSTEM

[75] Inventors: Kazumitsu Kobayashi; Masaru Kuribara, both of Atsugi, Japan

[73] Assignee: Unisia Jecs Corporation, Atsugi, Japan

[21] Appl. No.: 41,588

[22] Filed: Apr. 5, 1993

[30] Foreign Application Priority Data

Apr. 7, 1992 [JP] Japan .................. 4-114141

[51] Int. Cl.$^5$ .................. G01N 27/06; G01N 27/27; G01N 33/22; G01N 27/00
[52] U.S. Cl. .................. 364/497; 364/496; 324/690; 324/691; 73/61.41; 73/61.43
[58] Field of Search .................. 364/496, 497, 498, 499, 364/571.01, 571.02, 571.04, 571.07, 577; 73/61.43, 61.41, 61.44; 324/663, 690, 691; 340/450.02; 123/1 A

[56] References Cited

U.S. PATENT DOCUMENTS

| | | | |
|---|---|---|---|
| 4,470,300 | 9/1984 | Kobayashi | 73/61.43 X |
| 4,939,467 | 7/1990 | Noglami et al. | 73/61.41 X |
| 4,971,015 | 11/1990 | Gonze | 123/494 |
| 5,179,926 | 1/1993 | Ament | 73/61.43 X |
| 5,191,869 | 3/1993 | Kamioka et al. | 123/1 A X |
| 5,205,151 | 4/1993 | Shimamura et al. | 73/61.43 X |
| 5,216,409 | 6/1993 | Ament et al. | 340/450.02 X |

FOREIGN PATENT DOCUMENTS

4-8956  1/1992  Japan .

Primary Examiner—Jack B. Harvey
Assistant Examiner—Melanie A. Kemper
Attorney, Agent, or Firm—Foley & Lardner

[57] ABSTRACT

The fuel character judging system has an electrical capacitance type sensor which outputs a first detection signal representative of a first character of a fuel mixture. A resistance type sensor outputs a second detection signal representative of a second character of the fuel mixture. A control unit stores first and second maps for a known fuel mixture having known first, second and third numbers corresponding to components of the known fuel mixture. The first map has a plurality of first characteristic lines which respectively correspond to a plurality of values of the first detection signal from the electrical capacitance type sensor. The second characteristic lines are plotted in accordance with the second signal from the resistance type sensor upon changing the known first number. One of the second characteristic lines in the second map is selected in accordance with the first detection signal from the electrical capacitance type sensor. The unknown first number is determined in accordance with the one second characteristic line selected and with the second detection signal for the unknown fuel mixture, from the resistance type sensor. A first characteristic line in the first map is selected in accordance with the determined first unknown number. The unknown second number is determined in accordance with the selected first characteristic line and with the first detection signal for the unknown fuel mixture, from the electrical capacitance type sensor. The unknown third number is determined according to the first and second determined unknown numbers.

14 Claims, 11 Drawing Sheets

FUEL CHARACTER JUDGING SYSTEM

BACKGROUND OF THE INVENTION

1. Field of the Invention

This invention relates in general to improvements in a fuel character judging system for detecting the ratio of components in a fuel mixture to be supplied to an internal combustion engine, and more particularly to the fuel character judging system incorporated with a fuel injection system and arranged to judge the component ratio of a fuel mixture such as gasoline mixed with methanol and/or ethanol, or gasoline mixed with additives.

2. Description of the Prior Art

Recently, attention has been paid to fuel mixtures prepared by mixing alcohol (such as methanol) with gasoline, as fuel of automotive vehicles from view points of environmental protection and energy saving. However, such fuel mixtures are different in stoichiometric air-fuel ratio depending upon the concentration of alcohol contained in the gasoline. Accordingly, an alcohol concentration measuring device is necessarily used in a fuel supply line to measure the alcohol concentration in the fuel mixture. This alcohol concentration measuring device is used particularly for an internal combustion engine equipped with an electronically controlled fuel injection system including a fuel injector. The fuel supply amount of the fuel injector is regulated in accordance with the measured alcohol concentration in the fuel mixture.

The stoichiometric air-fuel ratio is 14.7 in the engine using a usual gasoline as fuel but is necessarily regulated to be 6.5 in an engine using methanol as fuel. Thus, the stoichiometric air-fuel ratio changes from 6.5 to 14.7 depending upon the alcohol concentration ranging from 0 to 100%. In view of the above, in case of using the gasoline-alcohol fuel mixture as fuel, the alcohol concentration measuring device called "alcohol sensor" is installed in the fuel supply line and adapted to generate an output voltage corresponding to the alcohol concentration. The fuel injection amount of the fuel injector is calculated in accordance with the output voltage from the alcohol concentration measuring device. A typical alcohol concentration measuring device is of the type of detecting the alcohol concentration in accordance with the dielectric constant of the fuel mixture.

Meanwhile, usual gasoline used as automotive fuel is classified into light, medium and heavy gasolines. The light gasoline contains paraffin hydrocarbons (such as heptane and pentane) as a main component and therefore tends to readily vaporize. The heavy gasoline contains aromatic hydrocarbons (such as benzene) as a main component and therefore tends to hardly vaporize. The medium gasoline has a character generally between the light and heavy gasolines. In usual automotive engines, the spark timing is set to match the light gasoline. When the heavy gasoline is used in these engines, a practical ignited timing of the fuel retards from the set spark timing of a spark plug, so that air-fuel mixture tendency is assumed totally lean. Thus, an engine operation on the heavy gasoline not only causes a degraded driveability due to discontinuous combustion or the like but also increases noxious exhaust gas components under incomplete combustion in the engine.

To solve such a problem, a gasoline character judging system has been proposed, for example, in a Japanese Utility Model Provisional Publication No. 4-8956. This gasoline character judging system includes an electrical capacitance detector having electrodes dipped in gasoline and adapted to detect the electrical capacitance between the electrodes which capacitance is determined depending on the character of the gasoline. An oscillator is provided to generate a frequency depending on the electrical capacitance detected by the electrical capacitance detector. A frequency-voltage converter is provided to convert the frequency from the oscillator to a voltage and output a voltage signal. The voltage value of the voltage signal from the frequency-voltage converter is compared with a predetermined voltage value, thereby judging as to whether the gasoline to be supplied to the engine is the light gasoline or the heavy gasoline.

The above-mentioned conventional alcohol concentration measuring device will be discussed further in detail.

The alcohol concentration measuring device can make an effective detection for alcohol concentration in case that only one kind of alcohol is mixed in gasoline. However, the following drawbacks have been encountered in the conventional alcohol concentration measuring device:

First, alcohols to be mixed with gasoline are considered to be typically ethanol and methanol. Besides, the following two cases are typically to exist: a case where ethanol or methanol is singly mixed with gasoline; the other case where ethanol and methanol are mixed together with gasoline. Ethanol and methanol are different in chemical structure and dielectric constant from each other. In this connection, ethanol, methanol and gasoline are respectively 32, 24 and 2 in dielectric constant. Accordingly, in case ethanol and methanol are mixed together with gasoline, the concentrations of ethanol and methanol are required to be independently detected. However, with the above alcohol concentration measuring device, the blended ratio of ethanol, methanol and gasoline cannot be detected.

Second, even in case that ethanol or methanol is singly mixed with gasoline, the same kind of alcohol is not always mixed with gasoline in which the electrical capacitance are differently affected respectively by ethanol and methanol because they are different in dielectric constant. As a result, it is impossible to detect the gasoline character by a single alcohol concentration measuring device.

Third, in case a gasoline containing two kinds of alcohols is mixed may be used in the automotive engine, it is impossible to accomplish appropriate fuel injection amount control and spark timing control since the stoichiometric air-fuel ratio and the practical ignited timing for the fuel mixture change with the blended ratio among the three components of the fuel mixture.

The above-mentioned conventional gasoline character judging system will be discussed further in detail.

Usual gasoline available on the market may includes alcohol contents such as methanol, ethanol, MTBE (metal tert-butyl ether) and/or the like, as additives. Accordingly, the dielectric constant of the usual gasoline is raised owing to the alcohol contents, and therefore the output voltage of the conventional gasoline character judging system is raised as the concentration of the additives is larger.

Accordingly, with the conventional gasoline character judging system arranged only to compare the output voltage with the predetermined voltage value, there is the possibility that the same voltage value is output from the frequency-voltage converter of the judging system in the following thee cases: a first case that the heavy gasoline is used; a second case that the medium gasoline containing additives is used; and a third case that the light gasoline containing additives is used. Thus, a precise judging of gasoline character is impossible according to measurement by such a conventional gasoline character judging system.

Additionally, the conventional gasoline character judging system is arranged to achieve the gasoline character judgment only for the gasoline of one kind. However, there are a variety of kinds of gasolines in practice, and therefore no precise gasoline character judgement is possible among different kinds of gasolines.

BRIEF SUMMARY OF THE INVENTION

It is an object of the present invention to provide an improved fuel character judging system for a fuel mixture to be used in an engine, which system is constructed and arranged to overcome the drawbacks encountered in conventional alcohol concentration measuring devices and gasoline character judging systems.

Another object of the present invention is to provide an improved fuel character judging system for a fuel mixture to be used in an engine, by which system an appropriate control of fuel injection amount and spark timing can be achieved even when an engine is operated on the mixture fuel or gasoline mixed with a plurality of alcohols or a plurality of additives.

A further object of the present invention is to provide an improved fuel character judging system for a fuel mixture to be used in an engine, which system can precisely detect a blended ratio of a plurality of components such as gasoline, alcohol(s) and additives in the mixture fuel.

A fuel character judging system according to the present invention is for a fuel and comprising a first sensor for detecting a first character of the fuel, disposed in the fuel. The first sensor is adapted to output a first detection signal representative of the first character. A second sensor is provided to detect a second character of the fuel. The second character is different from the first character. The second sensor is disposed in the fuel and adapted to output a second detection signal representative of the second character. A memory for memorizing first and second maps for a known fuel having known first, second and third numbers corresponding to components of the known fuel. The first map has a plurality of first characteristic lines which respectively correspond to a plurality of values of a known first number. The first characteristic lines are plotted in accordance with the first detection signal from the first sensor tipon changing the known second number. The second map has a plurality of second characteristic lines which respectively correspond to a plurality of values of the first detection signal from the first sensor. The second characteristic lines are plotted in accordance with the second signal from the second sensor tipon changing the known first number. Additionally, a fuel character judgement device is provided to judge not larger than three unknown numbers of an unknown fuel. The three unknown numbers are unknown first, second and third numbers which respectively correspond to the known first, second and third numbers. The fuel character judgement device includes a first selection device for selecting one of the second characteristic lines in the second map in accordance with the first detection signal from the first sensor. A first unknown number decision device forming part of the fuel character judgement device is provided to decide the unknown first number in accordance with the one second characteristic line selected by the first selection device and with the second detection signal for the unknown fuel, from the second sensor. A second selection device forming part of the fuel character judgment device is provided to select one of the first characteristic lines in the first map in accordance with the unknown first number decided by the first unknown number decision device. A second unknown number decision device forming part of the fuel character judgement device is provided to decide the unknown second number in accordance with the one first characteristic line selected by the second selection device and with the first detection signal for the unknown fuel, from the first sensor. Additionally, a third unknown number decision device forming part of the fuel character judgement device is provided to decide the unknown third number in accordance with the unknown first number decided by the first unknown number decision device and with the unknown second number decided by the second unknown number decision device.

With the above fuel character judging system, even in case the fuel has not larger than three unknown numbers, each unknown number can be precisely detected thereby judging the character of the fuel. The not larger than three unknown numbers may the concentration of first and second alcohols and gasoline, or kind of additive, the concentration of the additive and kind of gasoline. Accordingly, the fuel injection amount and spark timing in the engine is appropriately controlled maintaining a good driveability of the engine even if a fuel mixture having a variety of blended ratios of gasoline and alcohols.

BRIEF DESCRIPTION OF THE DRAWINGS

In the drawings, same reference numerals designate same elements and parts throughout all figures, in which.

DETAILED DESCRIPTION OF THE INVENTION

Figure 1:
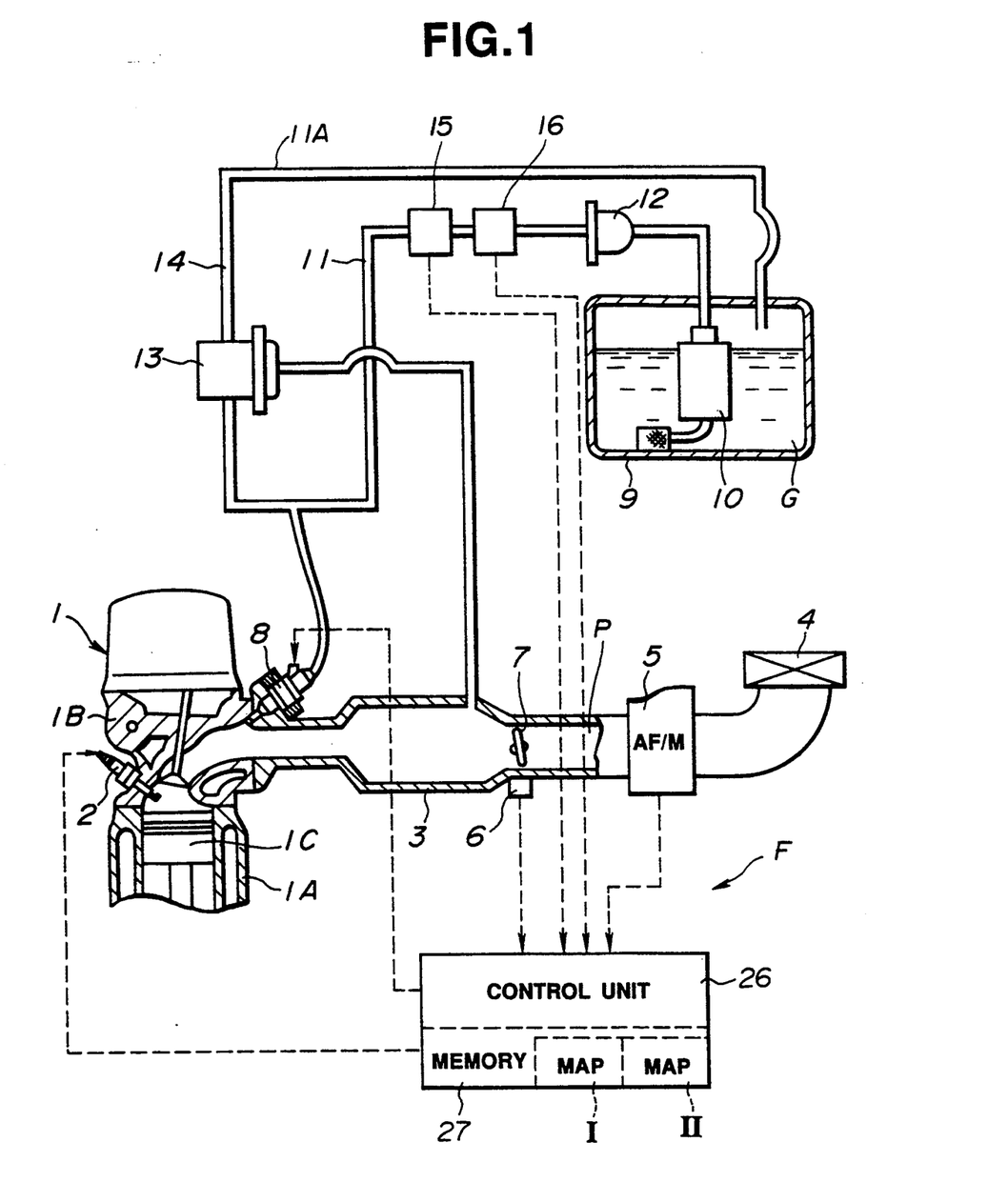
FIG. 1 is a schematic view, partly in section, of a first embodiment of a fuel character judging system according to the present invention.

Referring now to FIGS. 1 to 6, a first embodiment of a fuel character judging system of the present invention is illustrated by a reference character F and shown incorporated with an internal combustion engine 1 for an automotive vehicle (not shown). In this embodiment, the engine 1 has four engine cylinders one of which is shown in FIG. 1. The engine 1 includes a cylinder block 1A which is formed therein with the engine cylinders (not identified). A cylinder head 1B is fixedly mounted on the cylinder block 1A to define the engine cylinders. A piston 1C is reciprocally movably disposed in each engine cylinder. A spark plug 2 is provided for each engine cylinder and securely disposed to project in each engine cylinder. The spark plug 2 is adapted to fire air-fuel mixture in the engine cylinder in response to an ignition signal output from a control unit 26 which will be discussed after. Upon firing by the spark plug 2, the air-fuel mixture in the engine cylinder makes its combustion or explosion.

An intake manifold 3 is elisposed at the intake side of the cylinder head 1B and has branch runners each of which is connected with each engine cylinder which runners form a downstream part of the intake manifold 3. The intake manifold 3 is provided at its upstream end with an air filter 4 for filtering intake air sucked into the engine cylinders through the intake manifold 3. The intake manifold 3 is formed thereinside an intake air passage P through which intake air flows toward the engine cylinders. An air flow meter 5 is disposed near the air filter 4 and in the air flow passage P to measure the amount of intake air passing through the intake air passage P. A throttle valve 7 is movably disposed in the intake air passage P and located between the air flow meter 5 and the branch runners of the intake manifold 3. A throttle valve switch 6 is provided near and operatively connected with the throttle valve 7 to detect the throttle position (opening degree) of the throttle valve 7. A fuel injector valve 8 is fixedly disposed at each branch runner of the intake manifold 3 and located in close proximity to the cylinder head 1B. The fuel injector valve 8 is adapted to inject a fuel mixture into the intake air passage P in response to an ignition signal output from the control unit 26, so that the fuel mixture is mixed with intake air thereby to form an air-fuel mixture in the intake air passage P leading to the engine cylinders. Thus, each engine cylinder of the engine 1 is supplied with the air-fuel mixture to be cornbusted. In this embodiment, the fuel mixture is a mixture of gasoline with ethanol and methanol.

A fuel tank 9 is provided to store therein the fuel mixture, and provided thereinside with a fuel pump 10 for pumping the fuel mixture into a fuel supply line 11. The fuel supply line 11 is connected at its one end with the discharge side of the fuel pump 10 and at the other end with the fuel injector valve 8, so that the fuel injector valve 8 is supplied with the fuel mixture under pressure. A fuel filter 12 is disposed in the fuel supply line 11 near the fuel pump 10 in order to filter the fuel mixture. A pressure regulator 13 is disposed in a fuel return line 11A which is branched off from the fuel supply line 11 at a position near the fuel injector valve 8. In other words, the fuel return line 11A is connected at its one end with the fuel supply line 11 and at the other end with the fuel tank 9.

An electrical capacitance type sensor 15 is disposed in the fuel supply line 11 downstream of the fuel filter 12 and adapted to detect, as an electrical capacitance, a dielectric constant of the fuel mixture flowing in the fuel supply line 11, the dielectric constant depending on the character of the fuel mixture. A resistance type sensor 16 is disposed in the fuel supply line 11 and located upstream of the sensor 15. The resistance type sensor 16 is adapted to detect, as a resistance value, an electrical resistivity of the fuel mixture flowing through the fuel supply line 11, the electrical resistivity depending upon the character of the fuel mixture.

Figure 2:
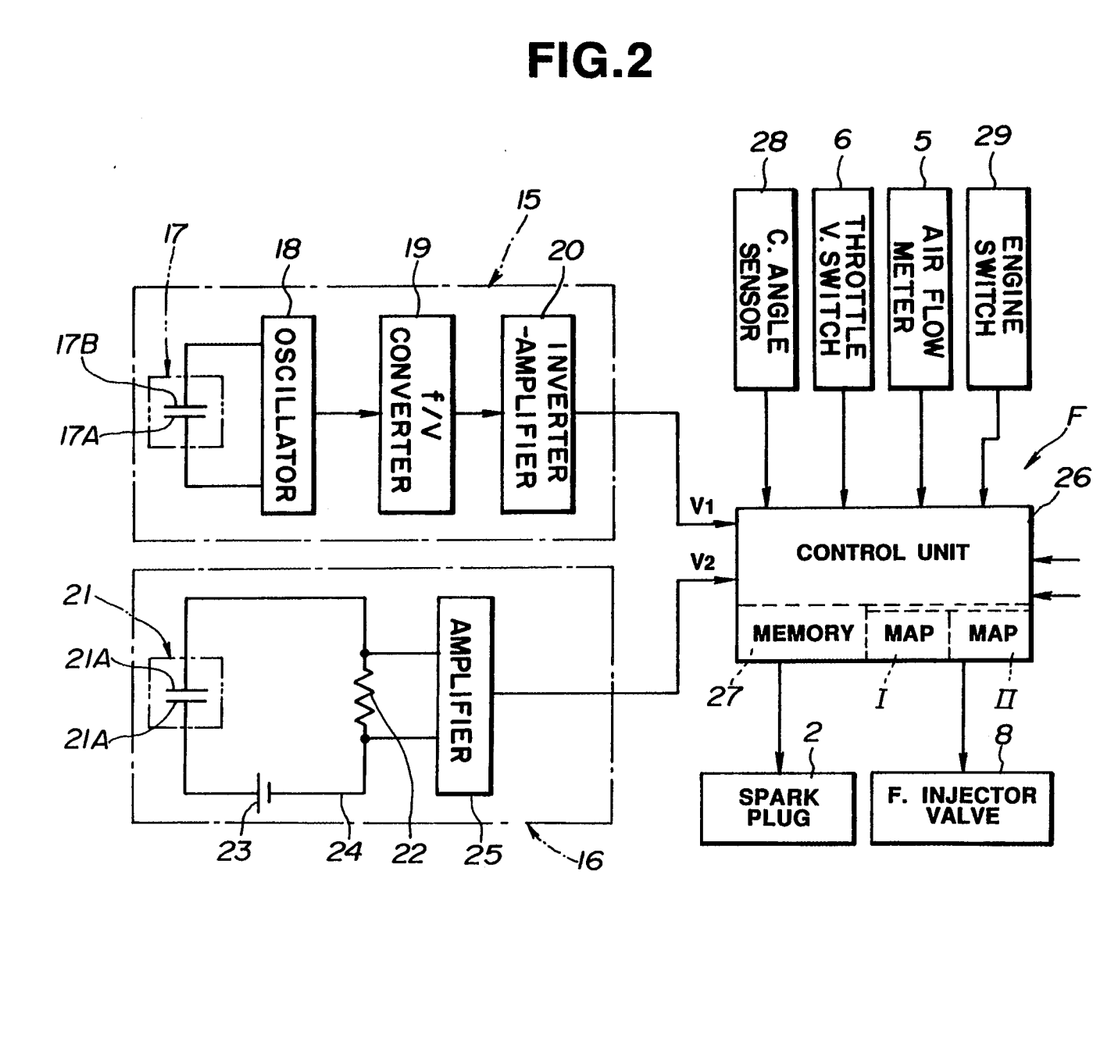
FIG. 2 is a circuit diagram of the fuel character judging system of FIG. 1.

As shown in FIG. 2, the electrical capacitance type sensor 15 includes a sensor section 17 having a pair of electrode plates 17A, 17B which are dipped in the fuel mixture flowing in the fuel supply line 11. The electrode plates 17A, 17B are formed flat and parallel with each other. The sensor section 17 is electrically connected to an oscillator 18 which is adapted to generate a frequency (signal) depending on the sensed electrical capacitance. The oscillator 18 is electrically connected to a frequency-voltage (f/v) converter 19 which is adapted to convert the frequency from the oscillator 18 into a voltage. The converter 19 is electrically connected to an inverter-amplifier 20 which is adapted to invert and amplify the voltage output from the f/v converter 19. Thus, the electrical capacitance type sensor 15 is arranged to output a detection voltage V1 corresponding to the dielectric constant depending upon the character of the fuel mixture, to the control unit 26.

The resistance type sensor 16 includes a sensor section 21 having a pair of electrode plates 21A, 21A which are dipped in the fuel mixture flowing through the fuel supply line 11. The electrode plates 21A, 21A are formed flat and parallel with each other. The electrode plates 21A, 21A form part of a series circuit 24 including a detection resistance 21 and a D.C. power source 23. The series circuit 24 is electrically connected to an amplifier 25 which is adapted to detect a change in voltage value at the detection resistance 22 as a change in current value at the series circuit and amplify this current value change. Thus, the resistance type sensor 16 is arranged to output a detection voltage V2 corresponding to the electrical resistivity depending on the character of the fuel mixture.

Figure 4:
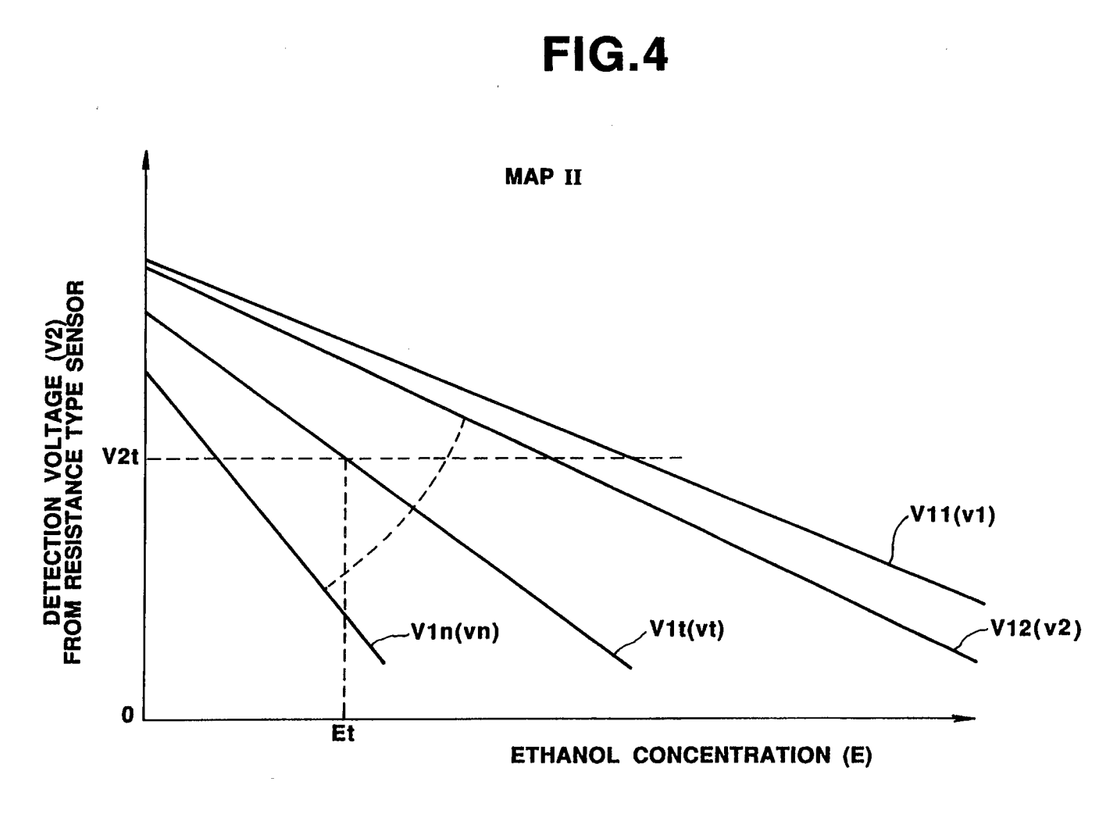
FIG. 4 is a graph of a characteristic map II used in the control of the first embodiment fuel character judging system.
Figure 5:
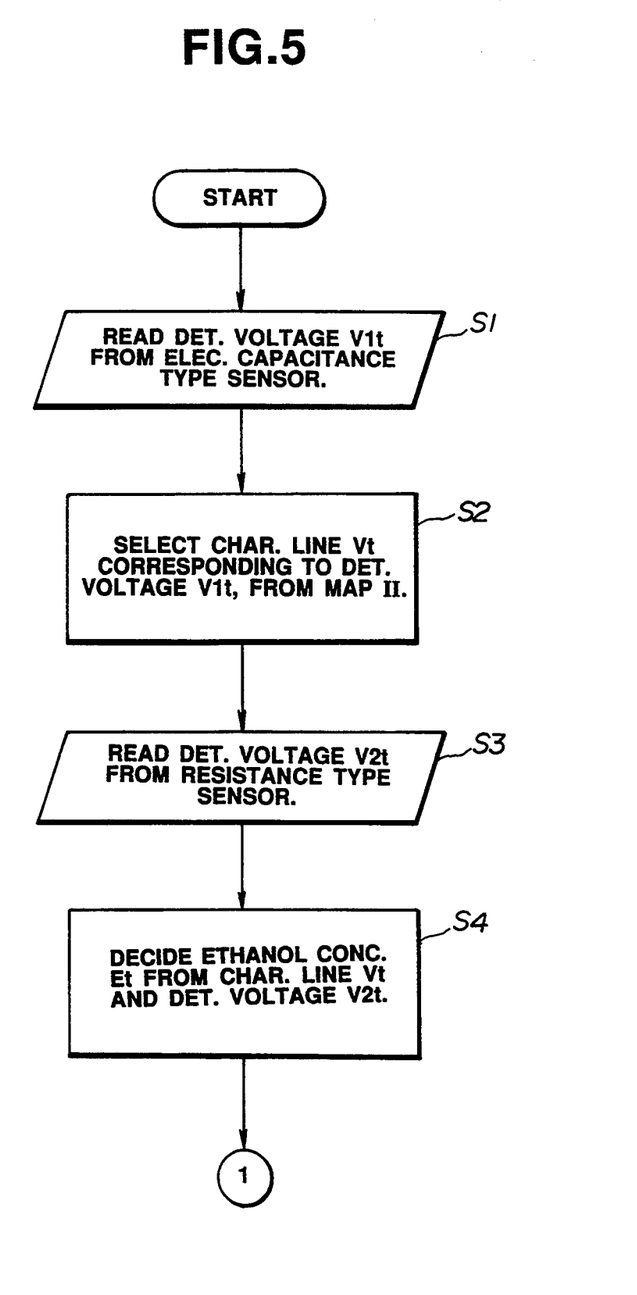
FIGS. 5 and 6 are flowcharts showing the control operation of the first embodiment fuel character judging system.
Figure 6:
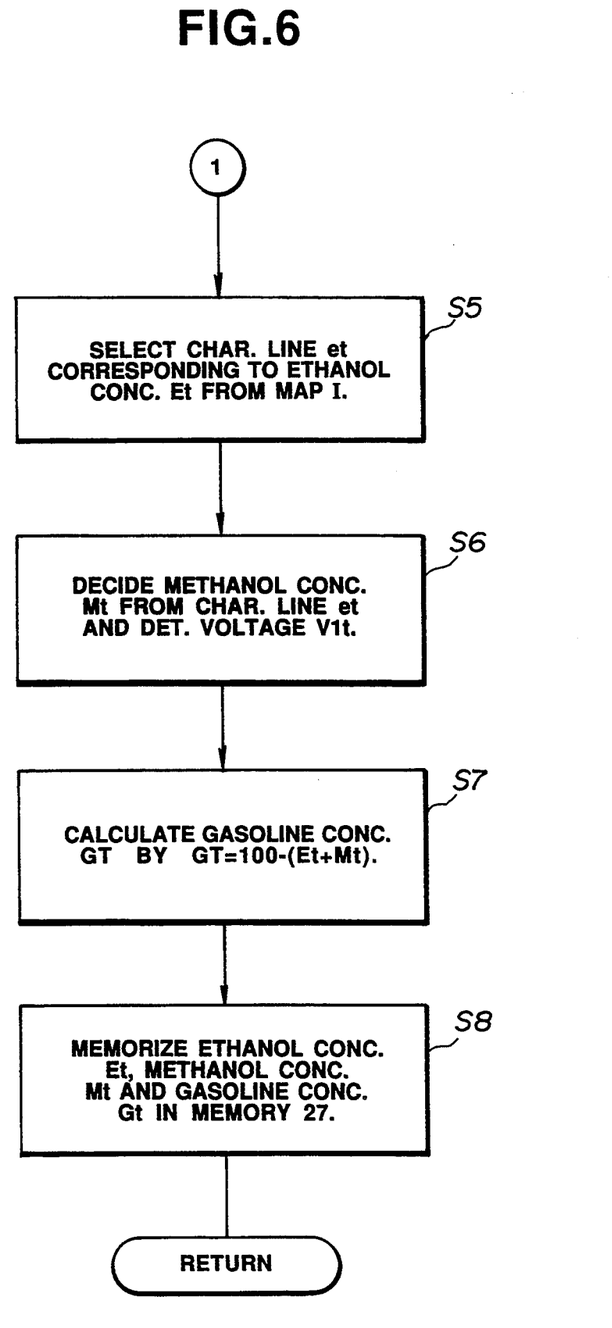

The control unit 26 is constituted of, for example, a microcomputer and the like, and includes a memory having RAM, ROM and the like. The control unit 26 stores therein a fuel character judging processing program as shown in FIGS. 5 and 6, and other programs such as a fuel injection amount calculating program (not shown) for calculating the amount of fuel to be injected through each fuel injector 8, and an ignition timing control program (not shown) for controlling the ignition or spark timing of each spark plug 2. Additionally, the memory 27 stores therein a characteristic map I shown in FIG. 3 and a characteristic map II shown in FIG. 4.

Electrically connected to the input side of the control unit 26 are the air flow meter 5 for outputting a signal representative of the air flow amount, the throttle valve switch 6 for outputting a signal representative of the throttle position, a crank angle sensor 28 for outputting a signal representative of the rotational angle of a crankshaft (not shown) of the engine for the purpose of detecting an engine speed, an engine switch 29 for outputting a signal representative of engine operation, and other sensors (not shown) such as an engine coolant temperature for outputting a signal representative of the temperature of engine coolant, and an oxygen sensor for outputting a signal representative of the concentration of oxygen in exhaust gas discharged from the engine cylinders of the engine 1. Additionally, the inverter-amplifier 20 of the electrical capacitance type sensor 15 and the amplifier 25 of the resistance type sensor 16 are electrically connected to the input side of the control unit 26. The spark plug 2, the fuel injector valve 8 and the like are electrically connected to the output side of the control unit 26.

Figure 3:
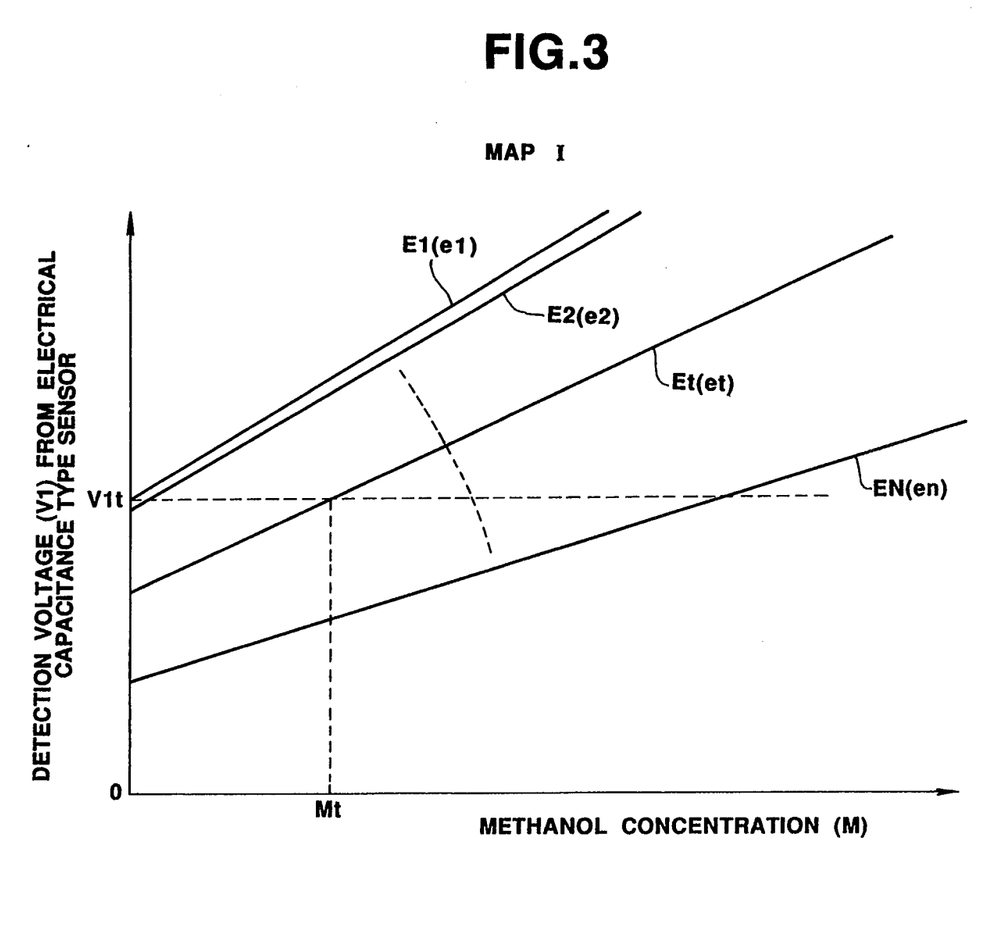
FIG. 3 is a graph of a characteristic map I used in a control of the first embodiment fuel character judging system.

The manner of preparation of the characteristic maps I and II will be discussed hereinafter.

First, many sample or known fuel mixtures are prepared in which each sample fuel mixture consists of gasoline in a concentration G (% by volume), methanol in a concentration M (% by volume) and ethanol in a concentration E (% by volume). In each sample fuel mixture, the total of the concentrations G, M, E (%) is 100%. In other words, each fuel mixture has three kinds of known numbers (G, M, E) which are usually unknown in fuel mixtures which are available on the market.

The thus prepared many sample fuel mixtures are subjected to measurement of dielectric constant by the electrical capacitance type sensor 15 thus obtaining the detection voltage V1. Similarly, the prepared many sample fuel mixtures are subjected to measurement of electrical resistivity by the resistance type sensor 16 thus obtaining the detection voltage V2. In accordance with the measured data, the characteristics maps I and II are formed.

In the characteristic map I, the known methanol concentration M is represented on the axis of abscissas while the detection voltage V1 (from the electrical capacitance type sensor 15) is represented on the axis of ordinates. According to the measuring data of the detection voltage V 1 on the above many sample fuel mixtures, a plurality of characteristic lines e1, e2 . . . et, . . . en are plotted respectively for ethanol concentrations E (E1, E2 . . . Et, . . . En) of the many sample fuel mixtures.

In the characteristic map II, the ethanol concentration E is represented on the axis of abscissas while the detection voltage V2 (from the resistance type sensor 16) is represented on the axis of ordinates. According to the measured data of the detection voltage V1 (from the electrical capacitance type sensor 15) and the detection voltage V2 on the above many sample fuel mixtures, a plurality of characteristic lines v1, v2 . . . vt, . . . vn are plotted respectively for values (V11, V12 . . . V1t, . . . V1n) of the detection voltage V1 of the many sample fuel mixtures.

Next, detection of the concentration of components of an unknown fuel mixture will be discussed with reference to a flowchart or program of FIGS. 5 and 6, in which the unknown fuel mixture is assumed to consist of ethanol in a concentration Et (an unknown first number), methanol in a concentration Mt (an unknown second number) mad gasoline in a concentration Gt (an unknown third number). It will be understood that the concentrations Et, Mt, Gt are unknown in fuel mixtures available on the market and therefore called the unknown numbers.

At a step S1, a value V1t of the detection voltage V1 is read from the electrical capacitance type sensor 15. At a step S2, the characteristic line vt corresponding to the read detection voltage V1t is selected in the characteristic map II. At a step S3, a value V2t of the detection voltage V2 is read from the resistance type sensor 16. At a step S4, the ethanol concentration Et is decided from the characteristic line vt and the detection voltage V2t as shown in FIG. 4.

At a step S5, the characteristic line et corresponding to the ethanol concentration Et decided at the step S4 is selected in the characteristic map I. At a step S6, the methanol concentration Mt is decided from the characteristic line et and the detection voltage V1t read at the step S1.

At a step S7, the gasoline concentration Gt is calculated according to the following equation:

$$Gt = 100 - (Et + Mt)$$

At a step S8, the ethanol concentration Et decided at the step S4, the methanol concentration Mt decided at the step S6 and the gasoline concentration decided at the step S7 are memorized in the memory 27 in the control unit 26. According to the thus memorized concentrations, the control unit 26 executes the fuel injection amount calculation program and the ignition timing control program stored in the memory 27.

As discussed above, according to this embodiment fuel character judging system of the present invention, the ethanol concentration Et and the methanol concentration Mt can be securely detected even in case ethanol and methanol are contained in the fuel mixture. Additionally, even in case ethanol or methanol is singly contained in gasoline, the ethanol or methanol concentration can be detected by this fuel character judging system.

Accordingly, by disposing the electrical capacitance type sensor 15 and the resistance type sensor 16 in the fuel supply line 11 and by carrying out the fuel character judging processing for deciding the respective concentrations as shown in FIGS. 5 and 6, the concentrations of ethanol and methanol in the fuel mixture can be precisely detected even if the concentrations are in any ratio, thereby accomplishing an appropriate control of fuel injection amount and ignition timing while improving driveability of the automotive vehicle.

FIGS. 7 to 11 illustrate a second embodiment of the fuel character judging system of the present invention, which is similar to the above embodiment of FIGS. 1 to 6 with the following exceptions. The electrode plates of the electrical capacitance type sensor and of the resistance type sensor are common thereby to form common electrode plates 35A, 35A to which a.c. and d.c. voltages are changeably applied. The electrode plates 35A, 35A form part of a sensor section 35 of the electrical capacitance type sensor 15' and of the resistance type sensor 16'. Additionally, one of two characteristic maps represents a variety of ethanol concentrations of the many sample fuel mixture in terms of the detection voltage (V3) from the resistance type sensor 16' and the methanol concentration (M), while the other map represents a variety of ethanol concentrations of the many sample fuel mixture in terms of the detection voltage (V4) from the electrical capacitance type sensor 15' and the ethanol concentration (E).

Figure 7:
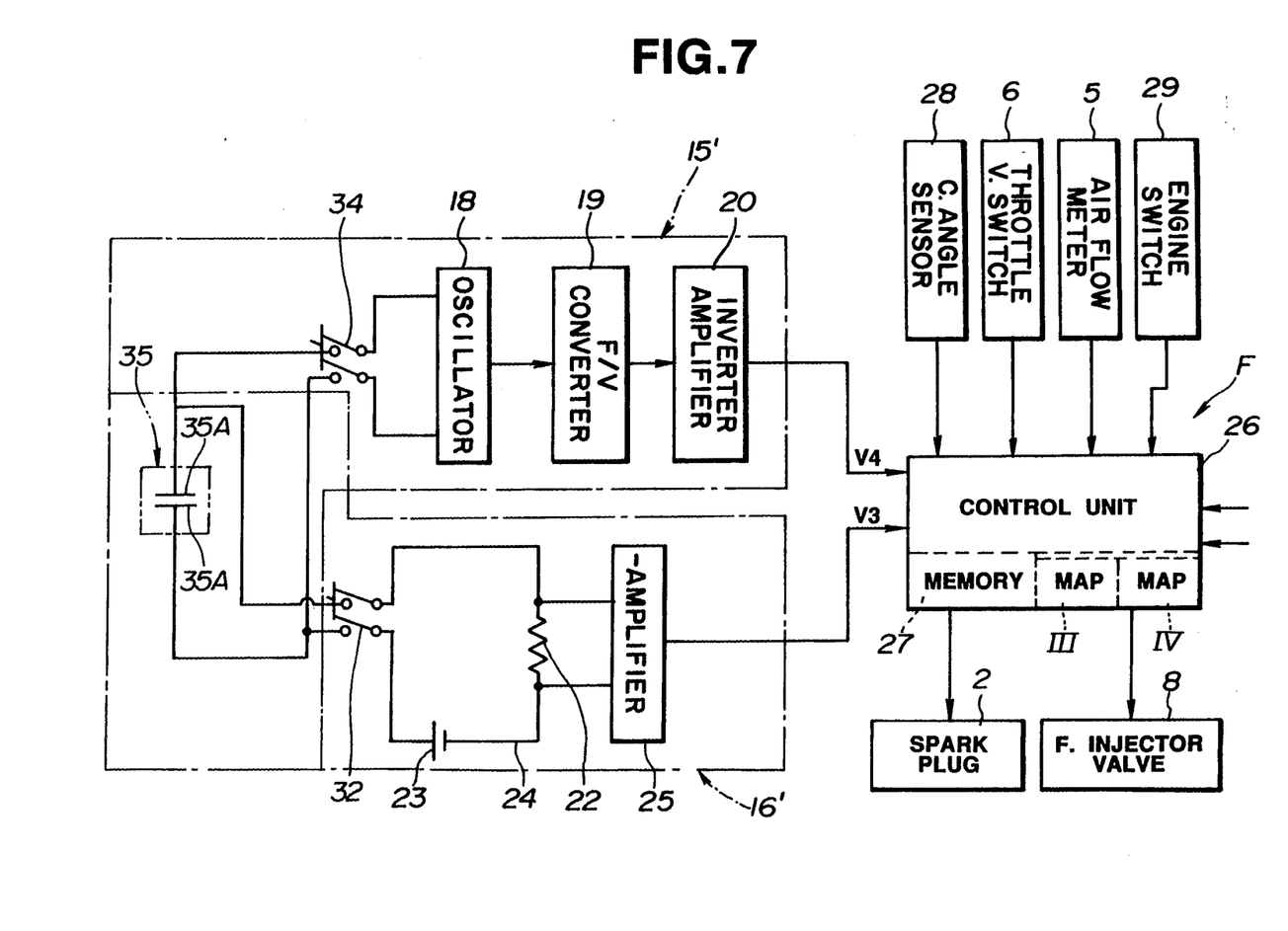
FIG. 7 is a circuit diagram similar to FIG. 2 but showing that of a second embodiment of the fuel character judging system in accordance with the present invention.

More specifically, the resistance type sensor 16' is similar to that 16 of the first embodiment and includes the series circuit 24 having the detection resistance 22 and the D.C. power source 23, and the amplifier 25. The series circuit 24 is electrically connected with the electrode plates 35A, 35A of the sensor section 35 through a switch 32. The electrical capacitance type sensor 15' is similar to that 15 of the first embodiment and includes the oscillator 18, the f/v converter 19 and the inverter-amplifier 20. The oscillator 18 is electrically connected with the electrode plates 35A, 35A of the sensor section 35 through a switch 34. The electrode plates 35A, 35A are dipped in the fuel mixture flowing in the fuel supply line 11. Thus, the resistance type sensor 16' is arranged to output a detection voltage V3, while the electrical capacitance type sensor 15' is arranged to output a detection signal V4.

Figure 9:
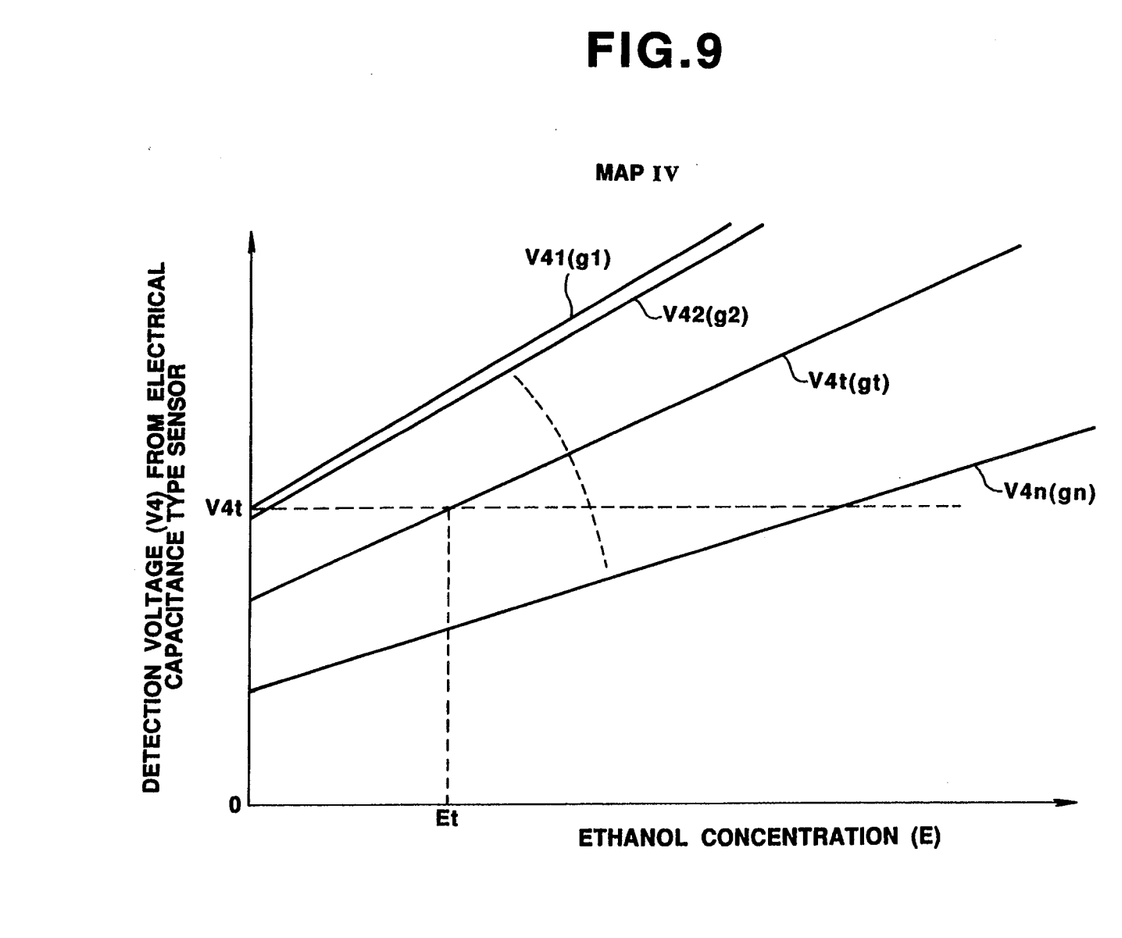
FIG. 9 is a graph of a characteristic map IV used in the control of the second embodiment fuel character judging system.
Figure 10:
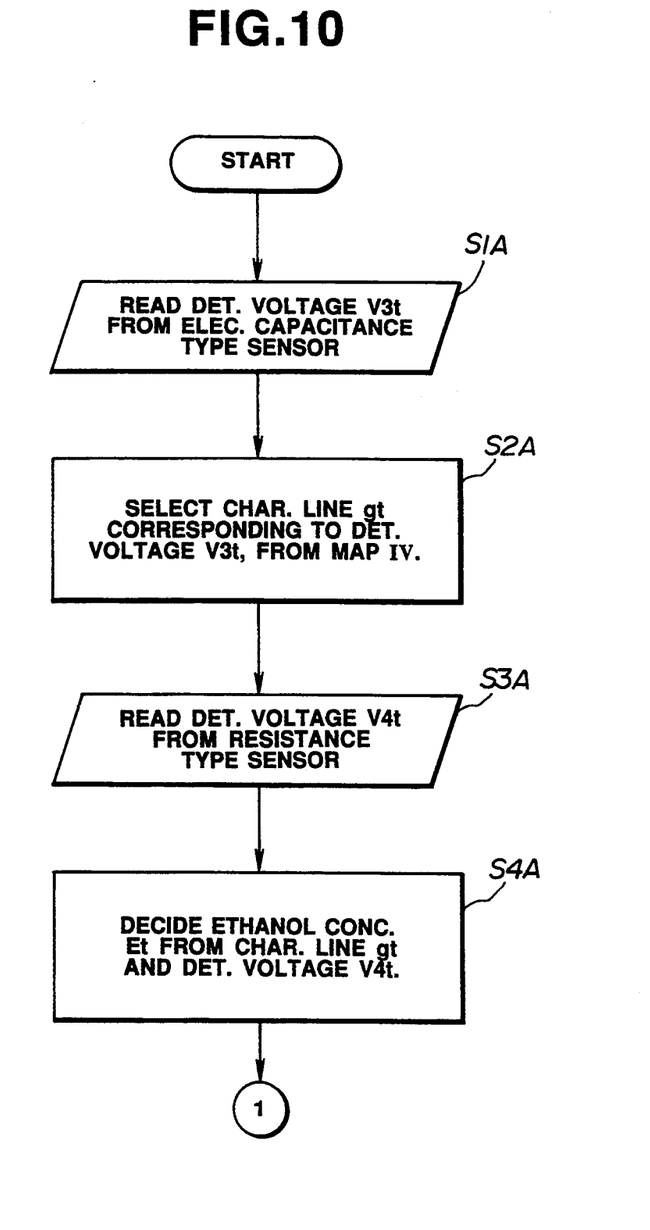
FIGS. 10 and 11 are flowcharts showing the control operation of the second embodiment fuel character judging system.
Figure 11:
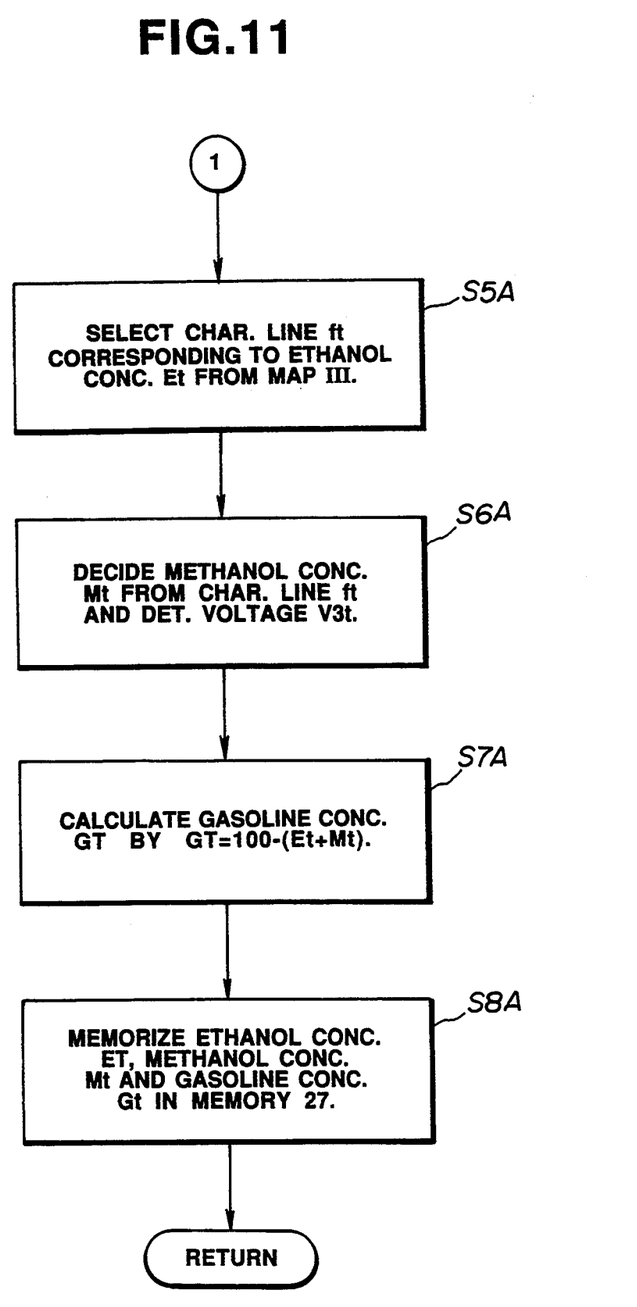

The control unit 26 is constituted of, for example, a microcomputer and the like, and includes a memory 27 having RAM, ROM and the like. The control unit 26 stores therein a character judging processing program as shown in FIGS. 10 and 11. Additionally, the memory 27 stores therein a characteristic map III shown in FIG. 8 and a characteristic map IV shown in FIG. 9. Each of the change-over switches 32, 34 is controlled to be closed or opened in response to a signal output from the control unit 36.

Figure 8:
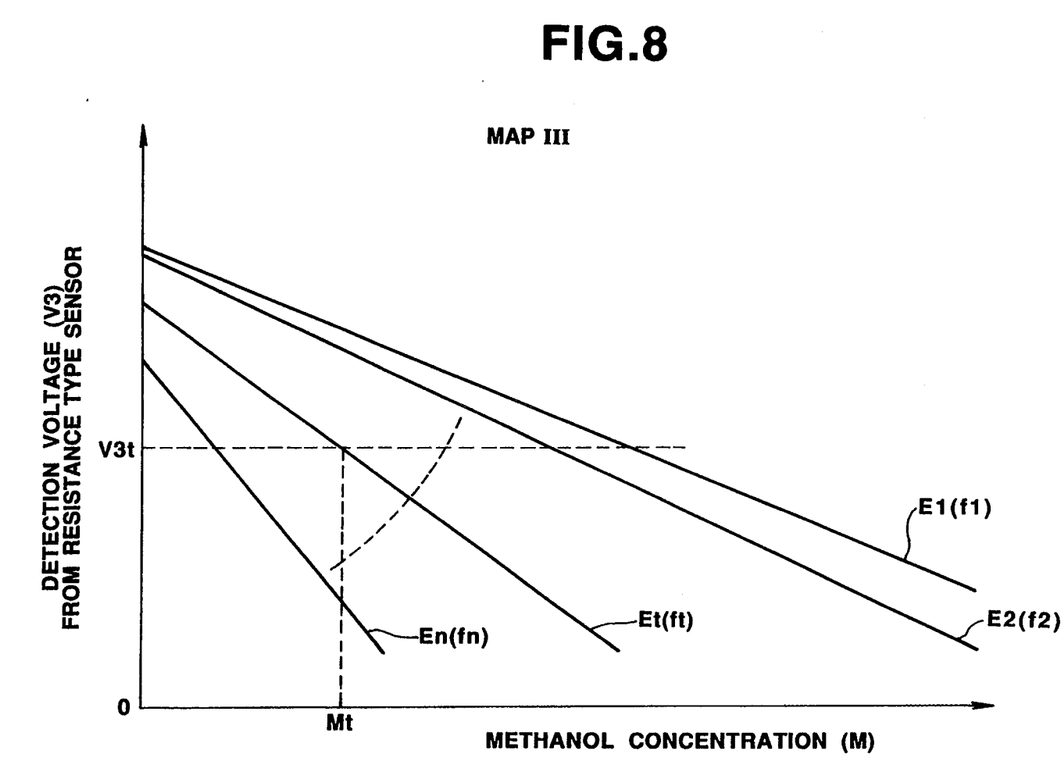
FIG. 8 is a graph of a characteristic map III used in a control of the second embodiment fuel character judging system.

With this arrangement, the characteristic maps III and IV will be prepared as follows:

First, many sample fuel mixtures are prepared in which each sample fuel mixture consists of gasoline in a concentration G (% by volume), methanol in a concentration M (% by volume) and ethanol in a concentration E (% by volume). In each sample fuel mixture, the total of the concentrations G, M, E (%) is 100%. In other words, each fuel mixture has three kinds of known numbers (G, M, E) which are usually unknown in fuel mixtures which are available on the market. The thus prepared many sample fuel mixtures are subjected to measurement of dielectric constant by the electrical capacitance type sensor 15' thus obtaining the detection voltage V4. Similarly, the prepared many sample fuel mixtures are subjected to measurement of electrical resistivity by the resistance type sensor 16' thus obtaining the detection voltage V3. In accordance with the measured data, the characteristic maps III and IV are formed.

In the characteristic map III, the known methanol concentration M is represented on the axis of abscissas while the detection voltage V3 (from the resistance type sensor 16') is represented on the axis of ordinates. According to the measuring data of the detection voltage V3 on the above many sample fuel mixtures, a plurality of characteristic lines f1, f2, . . . ft, . . . fn are plotted respectively for ethanol concentrations E (E1, E2 . . . Et, . . . En) of the many sample fuel mixtures. In the characteristic map IV, the known ethanol concentration E is represented on the axis of abscissas while the detection voltage V4 (from the electrical capacitance type sensor 15') is represented on the axis of ordinates. According to the measured data of the detection voltage V3 (from the resistance type sensor 16') and the detection voltage V4 on the above many sample fuel mixtures, a plurality of characteristic lines g1, g2 . . . gt, . . . gn are plotted respectively for values (V41, V42 . . . V4t, . . . V4n) of the detection voltage V4 of the many sample fuel mixtures.

Next, detection of the concentration of components of an unknown fuel mixture will be discussed with reference to a flowchart or program of FIGS. 10 and 11, in which the unknown fuel mixture is assumed to consist of ethanol in a concentration Et (the known first number), methanol in a concentration Mt (the known second number) and gasoline in a concentration Gt (the known third number). At a step S1A, a value V3t of the detection voltage V3 is read from the resistance type sensor 16'. At a step S2A, the characteristic line gt corresponding to the read detection voltage V3t is selected in the characteristic map IV. At a step S3A, a value V4t of the detection voltage V4 is read from the electrical capacitance type sensor 15'. At a step S4A, the ethanol concentration Et is decided from the characteristic line gt and the detection voltage V4t as shown in FIG. 9. At a step SSA, the characteristic line ft corresponding to the ethanol concentration Et decided at the step S4A is selected in the characteristic map III. At a step S6A, the methanol concentration Mt is decided from the characteristic line ft and the detection voltage V3t read at the step S1A. At a step S7A, the gasoline concentration Gt is calculated according to the following equation: $Gt = 100 - (Et + Mt)$. At a step S8A, the ethanol concentration Et decided at the step S4A, the methanol concentration Mt decided at the step S6A and the gasoline concentration Gt decided at the step S7A are memorized in the memory 27 in the control unit 26. According to the thus memorized concentrations, the control unit 26 executes the fuel injection amount calculation program and the ignition timing control program stored in the memory 27.

Thus, even with this embodiment fuel character judging system, the ethanol concentration Et, the methanol concentration Mt and the gasoline concentration Gt in the fuel mixture can be securely decided. Additionally, the sensor section 35 is commonly used for the electrical capacitance type sensor 15' and for the resistance type sensor 16', and therefore the number of joint sections in the fuel supply line 11 is reduced as compared with the first embodiment fuel character judging system thereby contributing to prevent fuel leak or the like in the fuel supply line 11.

While the above discussed embodiments have been shown and described as carrying out the processing to detect the ethanol concentration Et, the methanol concentration Mt and the gasoline concentration Gt as the unknown numbers, it will be understood that the unknown numbers to detected is not be limited to them. The unknown number may be a kind of fuel additive, concentration of the fuel additive, or kind of gasoline (for example, heavy gasoline or light gasoline). Even in this case, the kind of fuel additive, the concentration of the fuel additive and/or the kind of gasoline as the unknown numbers can be securely detected by preparing characteristic maps like those I and II (III and IV) and carrying out a processing similar to that in the above embodiments. It will be understood that the above-mentioned heavy gasoline contains aromatic hydrocarbons (such as benzene) as a main component, while the light gasoline contains paraffin hydrocarbons (such as heptane and pentane) as a main component.

Although the electrode plates 17A, 17B; 21A, 21A; 35A, 35A of the sensor section 17, 21, 35 have been shown and described as being of the flat and parallel type in the above discussed embodiments, it will be appreciated that the electrode plates may be of the coaxial and cylindrical type.

While the sensor sections 17, 21 (35) of the electrical capacitance type sensor 15 (15') and the resistance type sensor 16 (16') have been shown and described as being disposed in the fuel supply line 11, it will be understood that each of the sensor sections 17, 21 may be disposed in the fuel tank 9.

It will be appreciated that if the detection voltages V1, V3 at the sensors 15, 15' do not exist respectively on the characteristic lines e1 to en and the characteristic lines f1 to fn, an intermediate characteristic line between the shown characteristics lines can be selected by using an interpolation, thereby making possible to detect a variety of unknown numbers.

While the above discussed embodiments have been shown and described as being arranged such that the electrical capacitance type sensor 15 (15') outputs the detection voltage V1 (V4) corresponding to the dielectric constant of the fuel mixture, and the resistance type sensor 16 (16') outputs the detection voltage V2 (V3) corresponding to the electrical resistivity of the fuel mixture, it will be understood that the electrical capacitance type sensor 15 (15') may be adapted to output a detection signal representative of dielectric constant or electrical capacitance, and the resistance type sensor 16 (16') may be adapted to output a detection signal representative of electrical resistivity or resistance value.

What is claimed is:

1. A fuel character judging system for a fuel, comprising:

a first sensor for detecting a first character of the fuel, disposed in the fuel, said first sensor being adapted to output a first detection signal representative of the first character;

a second sensor for detecting a second character of the fuel, the second character being different from the first character, said second sensor being disposed in the fuel and adapted to output a second detection signal representative of the second character;

memory means for memorizing first and second maps for a known fuel having known first, second and third numbers corresponding to components of the known fuel, said first map having a plurality of first characteristic lines which respectively correspond to a plurality of values of a known first number, said first characteristic lines being plotted in accordance with the first detection signal from said first sensor upon changing the known second number, said second map having a plurality of second characteristic lines which respectively correspond to a plurality of values of the first detection signal from said first sensor, the second characteristic lines being plotted in accordance with the second signal from said second sensor upon changing the known first number; and fuel character judgement means for judging not larger than three unknown numbers of an unknown fuel, said three unknown numbers being unknown first, second and third numbers which respectively correspond to the known first, second and third numbers, said fuel character judgement means including first selection means for selecting one of the second characteristic lines in the second map in accordance with the first detection signal from said first sensor, first unknown number decision means for deciding the unknown first number in accordance with the one second characteristic line selected by said first selection means and with the second detection signal for the unknown fuel, from said second sensor, second selection means for selecting one of the first characteristic lines in the first map in accordance with the unknown first number decided by said first unknown number decision means, second unknown number decision means for deciding the unknown second number in accordance with the one first characteristic line selected by said second selection means and with the first detection signal for the unknown fuel, from said first sensor, and third unknown number decision means for deciding the unknown third number in accordance with the unknown first number decided by said first unknown number decision means and with the unknown second number decided by said second unknown number decision means.

2. A fuel character judging system as claimed in claim 1, wherein said first sensor is an electrical capacitance type sensor, and said second sensor is a resistance type sensor.

3. A fuel character judging system as claimed in claim 1, wherein said first sensor is a resistance type sensor, and a second sensor is an electrical capacitance type sensor.

4. A fuel character judging system as claimed in claim 1, wherein said first map includes values of the known second number on axis of abscissa, and values of the first signal from said first sensor on axis of ordinates.

5. A fuel character judging system as claimed in claim 4, wherein said second map includes values of the known first number on axis of abscissa, and values of the second signal from said second sensor on axis of ordinates.

6. A fuel character judging system as claimed in claim 1, wherein said first map includes values of the known second number on axis of abscissa, and values of the second signal from said second sensor on axis of ordinates.

7. A fuel character judging system as claimed in claim 6, wherein said second map includes values of the known first number on axis of abscissa, and values of the first signal from said first sensor on axis of ordinates.

8. A fuel character judging system as claimed in claim 1, wherein said first sensor and said second sensor have common electrodes to which a.c. voltage and d.c. voltage are changeably impressed, said electrodes being disposed in the fuel.

9. A fuel character judging system as claimed in claim 1, wherein said first, second and third numbers are respectively concentrations of first alcohol, second alcohol and gasoline, said first alcohol being different from said second alcohol.

10. A fuel character judging system as claimed in claim 1, wherein said first, second and third numbers are respectively numbers representative of a kind of an additive, concentration of the additive and kind of gasoline.

11. A fuel character judging system for a fuel mixture, comprising:

an electrical capacitance type sensor for detecting a first character of the fuel mixture, disposed in the fuel mixture, said electrical capacitance type sensor being adapted to output a first detection signal representative of the first character;

a resistance type sensor for detecting a second character of the fuel mixture, the second character being different from the first character, said resistance type sensor being disposed in the fuel mixture and adapted to output a second detection signal representative of the second character;

memory means for memorizing first and second maps for a known fuel mixture having known first, second and third numbers corresponding to components of the known fuel mixture, said first map having a plurality of first characteristic lines which respectively correspond to a plurality of values of the known first number, said first characteristic lines being plotted in accordance with the first detection signal from said electrical capacitance type sensor upon changing the known second number, said first map including values of the known second number on axis of abscissa, and values of the first signal from said electrical capacitance type sensor on axis of ordinates, said second map having a plurality of second characteristic lines which respectively correspond to a plurality of values of the first detection signal from said electrical capacitance type sensor, the second characteristic lines being plotted in accordance with the second signal from said resistance type sensor upon changing the known first number, said second map including values of the known first number on axis of abscissa, and values of the second signal from said resistance type sensor; and fuel mixture character judgement means for judging not larger than three unknown numbers of an unknown fuel mixture, said three unknown numbers being unknown first, second and third numbers which respectively correspond to the known first, second and third numbers, said fuel mixture character judgement means including, first selection means for selecting one of the second characteristic lines in the second map in accordance with the first detection signal from said electrical capacitance type sensor, first unknown number decision means for deciding the unknown first number in accordance with the one second characteristic line selected by said first selection means and with the second detection signal for the unknown fuel mixture, from said resistance type sensor, second selection means for selecting one of the first characteristic lines in the first map in accordance with the first unknown number decided by said first unknown number decision means, second unknown number decision means for deciding the unknown second number in accordance with the one first characteristic line selected by said second selection means and with the first detection signal for the unknown fuel mixture, from said electrical capacitance type sensor; and third unknown number decision means for deciding the unknown third number in accordance with the unknown first number decided by said first unknown number decision means and with the unknown number second decided by said second unknown number decision means.

12. A fuel character judging system for a fuel mixture, comprising:

a resistance type sensor for detecting a first character of the fuel mixture, disposed in the fuel mixture, said resistance type sensor being adapted to output a first detection signal representative of the first character;

an electrical capacitance type sensor for detecting a second character of the fuel mixture, the second character being different from the first character, said electrical capacitance type sensor being disposed in the fuel mixture and adapted to output a second detection signal representative of the second character;

memory means for memorizing first and second maps for a known fuel mixture having known first, second and third numbers corresponding to components of the known fuel mixture, said first map having a plurality of first characteristic lines which respectively correspond to a plurality of values of the known first number, said first characteristic lines being plotted in accordance with the first detection signal from said resistance type sensor upon changing the known second number, said first map including values of the known second number on axis of abscissa, and values of the first signal from said resistance type sensor on axis of ordinates, said second map having a plurality of second characteristic lines which respectively correspond to a plurality of values of the first detection signal from said resistance type sensor, the second characteristic lines being plotted in accordance with the second signal from said electrical capacitance type sensor upon changing the known first number, said second map including values of the known first number on axis of abscissa, and values of the second signal from said electrical capacitance type sensor on axis of ordinates; and fuel mixture character judgement means for judging not larger than three unknown numbers of an unknown fuel mixture, said three unknown numbers being unknown first, second and third numbers which respectively correspond to the known first, second and third numbers, said fuel mixture character judgement means including, first selection means for selecting one of the second characteristic lines in the second map in accordance with the first detection signal from said first sensor, first unknown number decision means for deciding the unknown first number in accordance with the one second characteristic line selected by said first selection means and with the second detection signal for the unknown fuel mixture, from said second sensor, second selection means for selecting one of the first characteristic lines in the first map in accordance with the unknown first number decided by said first unknown number decision means, second unknown number decision means for deciding the unknown second number in accordance with the one first characteristic line selected by said second selection means and with the first detection signal for the unknown fuel mixture, from said resistance type sensor sensor, and third unknown number decision means for deciding the unknown third number in accordance with the unknown first number decided by said first unknown number decision means and with the unknown second number decided by said second unknown number decision means.

13. A method for judging fuel character of a fuel, comprising the steps of:

detecting a first character of the fuel using a first sensor disposed in the fuel, said first sensor outputting a first detection signal representative of the first character;

detecting a second character of the fuel using a second sensor, said second character being different from said first character, said second sensor being disposed in said fuel and outputting a second detection signal representative of said second character;

storing in a memory first and second maps for known fuels having known first, second and third parameters corresponding to components of the known fuel, said first map having a plurality of first characteristic lines which respectively correspond to a value of said known first parameter, said first characteristic lines being plotted in accordance with the first detection signal from said first sensor for a range of values of the known second parameter, said second map having a plurality of second characteristic lines which respectively correspond to a value of the first detection signals from said first sensor, the second characteristic lines being plotted in accordance with the second signal from said second sensor for a range of values of said known first parameter;

selecting one of the second characteristic lines in the second map in accordance with the first detection signal from said first sensor;

determining an unknown first parameter representing a first component of said unknown fuel in accordance with said one second characteristic line and with the second detection signal from the unknown fuel from said second sensor, selecting one of the first characteristic lines in the first map in accordance with the determined unknown first parameter;

determining an unknown second parameter representing a second component of said unknown fuel in accordance with the one first characteristic line selected and with the first detection signal from the unknown fuel from said first sensor; and determining an unknown third parameter representing a third component of said unknown fuel in accordance with the determined unknown first parameter and with the determined unknown second parameter.

14. The method according to claim 13 wherein said first parameter is ethanol concentration, said second parameter is methanol concentration and said third parameter is gasoline concentration.

* * * * *